United States Patent [19]

Prevorsek et al.

[11] 4,165,634
[45] Aug. 28, 1979

[54] VISCOELASTOMETER AND PROCESS FOR MEASURING VISCOELASTIC PROPERTIES

[75] Inventors: Dusan C. Prevorsek; Young D. Kwon; Raj K. Sharma, all of Morristown, N.J.

[73] Assignee: Allied Chemical Corporation, Morris Township, Morris County, N.J.

[21] Appl. No.: 875,712

[22] Filed: Feb. 6, 1978

[51] Int. Cl.² ............................................. G01N 3/32
[52] U.S. Cl. ........................................ 73/810; 73/830
[58] Field of Search .................... 73/91, 100, 95, 15.6, 73/808, 830

[56] References Cited

U.S. PATENT DOCUMENTS

| | | | |
|---|---|---|---|
| 3,969,930 | 7/1976 | Prevorsek et al. | 73/91 |
| 4,056,973 | 11/1977 | Prevorsek et al. | 73/91 |

Primary Examiner—Anthony V. Ciarlante
Attorney, Agent, or Firm—Robert J. North; Robert A. Harman

[57] ABSTRACT

An improved apparatus and process are described for measuring linear and non-linear viscoelastic properties of viscoelastic materials such as nylon, polyester tire cord, rubber, rubber-tire cord composites and the like. The properties are determined by subjecting a sample material to a constant-rate strain displacement having a small amplitude high frequency sinusoidal strain displacement superimposed thereon, and analyzing the overall resulting material stress. The obtained properties can be used to predict and estimate actual end use characteristics of the material such as longevity and mechanical loss during performance. In the case of tire cord, this latter characteristic can be surprisingly related to efficiency of fuel consumption in automotive vehicles.

29 Claims, 10 Drawing Figures

VISCOELASTOMETER AND PROCESS FOR MEASURING VISCOELASTIC PROPERTIES

BACKGROUND OF THE INVENTION

1. Field of the Invention

This invention relates to an improved apparatus and process for measuring linear and non-linear viscoelastic properties of viscoelastic materials.

2. Brief Description of the Prior Art

Commonly assigned U.S. Pat. No. 3,969,930 (Prevorsek et al. to Allied Chemical, 1976) discloses an apparatus and method for applying a known sinusoidal strain wave to a viscoelastic material and measuring the resulting stress in the material as a function of the applied cyclic strain. By this method, the overall total modulus of the material can be measured, and the mechanical loss, associated with the expansion-contraction cycle under non-linear viscoelastic conditions, can be determined from the area within the characteristic stress-strain hysteresis loop of the material.

Commonly assigned U.S. Pat. No. 4,056,973, (Prevorsek et al. to Allied Chemical, 1976) discloses an apparatus and method for applying a composite strain wave, comprised of a high frequency small amplitude sinusoidal strain wave superimposed onto a low frequency large amplitude fundamental sinusoidal strain wave, to a viscoelastic material, and measuring the resulting stress in the material as a function of the applied cyclic strain. By this method, the instantaneous modulus of the material can be obtained, from which conclusions can be drawn regarding; (a) the instantaneous mechanical loss as a function of applied cyclic strain, and (b) factors affecting the shape and area of the resulting stress wave or stress-strain hysteresis loop. These data provide useful information in analyzing the performance of viscoelastic structural parts in actual end uses as for example, polymeric tire cord in a rolling automobile tire, and can lead to estimates of tire temperature profiles during service and tire rolling resistance, which in turn is ultimately and quite surprisingly related to efficiency of fuel consumption in automotive vehicles.

The above-identified references describe the analysis of resulting stress in a viscoelastic material when subjected to large amplitude fundamental sinusoidal strain waves. Under these conditions, where the applied cyclic strain is continuously varying, the material usually exhibits non-linear viscoelastic behavior.

However, the above-identified references do not disclose methods or apparatus for determining the dependence of mechanical loss upon the applied strain during applied constant rate strain for a viscoelastic material, nor for determining the instantaneous modulus during testing-to-rupture, or tensile testing, of such a material.

When a viscoelastic material is subjected to sinusoidal deformation under prestrain, the strain $\gamma$ varies according to the expression:

$$\gamma(\theta) = \gamma_o + \Delta\gamma \sin \theta \qquad (1)$$

wherein $\gamma_o$ is prestrain, $\Delta\gamma$ is the strain amplitude and $\theta$ is the angle during the cycle varying from 0° to 360°.

When the strain amplitude is very small, the resulting stress wave is also sinusoidal but shifted on the angle scale by the phase angle difference $\delta$ so that stress $\sigma$ is represented by the expression $$\sigma(\theta) = \sigma_o + \Delta\sigma \sin(\theta + \delta) \qquad (2)$$

In this case, $\delta$ and $\Delta\sigma$ are independent of $\theta$. The ratio $\Delta\sigma/\Delta\gamma$ represents the complex modulus $E^*$, while phase angle difference is related to the mechanical loss during the cycle. Each $E^*$ and $\delta$ are important characteristics of viscoelastic materials. At very low strain amplitudes, the viscoelastic properties $E^*$ and $\delta$, are independent of the strain amplitude. Materials which under cyclic strain obey equation (2), are referred to as being linear viscoelastic.

When the strain amplitude is increased, there is observed, with all viscoelastic materials, a strain amplitude at which equation (2) no longer accurately describes the stress during the cycle. The stress wave resulting from the large amplitude sinusoidal strain wave is distorted and non-sinusoidal, and equation (2) assumes the form $$\sigma(\theta) = \sigma_o + \Delta\sigma(\theta) \sin[\theta + \delta(\theta)]. \qquad (3)$$

The resulting viscoelastic properties such as dynamic modulus, mechanical loss, and the like, are then strain dependent, and the strain amplitude at which this occurs is often referred to as the limit of linear viscoelastic response. Above this limit, various materials, for example, polymeric devices (such as heart valves) and reinforced composites (such as pneumatic tires) are subjected to deformation exceeding linear response and thus exhibit non-linear viscoelastic behavior. The performance of these polymers as parts or components in actual end use under these conditions, can be correlated to the shape and area of the stress-strain hysteresis loop or stress response wave by the methods described in the above-identified references. The methods are directed to determining $\Delta\sigma(\theta)$ and $\delta(\theta)$, which involve superimposing a high frequency small amplitude strain wave onto a fundamental large amplitude low frequency wave, and determining the changes in modulus as a function of strain (or angle $\Lambda$) during the cycle and also constructing the non-linear elastic stress wave. By the term, "non-linear elastic stress wave, is meant the wave form that is calculated from the instantaneous modulus in the non-linear viscoelastic region of the stress response wave.

The instantaneous modulus is derived by superimposing a small strain amplitude (less than 1%) high frequency sinusoidal wave onto the fundamental sinusoidal wave and determining the resulting stress. By the term "strain amplitude" is meant the quantity $\Delta L/L$, where $\Delta L$ is the displacement amplitude, and $L$ is the length of the sample under pretension at the beginning of the testing procedure. The non-linear elastic stress value is then calculated from the instantaneous modulus and the fundamental strain wave. The difference in the angle between the observed stress and the calculated nonlinear elastic stress is given the symbol, $\delta'$, and represents the mechanical loss of a viscoelastic material under nonlinear viscoelastic conditions during an expansion-contraction cycle. When non-linear viscoelastic stress is plotted as the ordinate versus observed strain as the abscissa, a stress-strain hysteresis loop results indicating mechanical loss during the cycle, and the area of the hysteresis loop is dependent on $\delta'$, a measure of mechanical loss during the cycle. Plots of $\delta'$ as function of $\theta$ during applied cyclic strain, by use of the apparatus and methods of the above-identified references, show that frequently $\delta'$ exhibits maxima at $\theta = 0°$ and 180°, which suggests that with many materials $\delta'$ may be strainrate dependent.

Thus, an apparatus and process are needed for determining whether $\delta'$, and thus the shape and area of the hysteresis loop for a viscoelastic material, is affected by changes in strain rate during periodic experiments.

It would also be very desirable to measure changes in viscoelastic properties under the conditions employed in standard tensile tests. These tests are frequently carried out at constant strain rate until the specimen ruptures, but information concerning the instantaneous modulus during these processes is not readily obtainable.

SUMMARY OF THE INVENTION

We have unexpectedly found that by applying a constant rate fundamental strain displacement to a viscoelastic material, having high frequency low amplitude sinusoidal displacement superimposed thereon, the dependence of the mechanical loss, $\delta'$, as a function of the applied strain rate for a viscoelastic material can be determined. Furthermore, we have found that by conducting the above process in a non-periodic manner, such that the constant strain displacement, having a superimposed high frequency low amplitude sinusoidal displacement thereon, is applied unidirectionally until sample rupture, the instantaneous modulus of the material can be measured at any given point of applied strain.

By the term "constant rate" is meant the rate at which strain is applied and can be unidirectionally linear, preferably in an increasing manner such as during an expansion, or periodically increasing or decreasing by a constant time factor, such as in an expansion-contraction cycle where the time required for expansion is equal to the time required for contraction, the total cycle constituting one period, which is continuously reproduced.

In accordance with this invention there is provided an improved apparatus for testing a viscoelastic material including:

(a) holding means connected to the material for holding the material in a predetermined position during testing;

(b) pretension means coupled to the material for applying tension to the material during testing;

(c) a first displacement generator having an eccentric means coupled to the material for applying cyclic displacement to the material; and (d) mechanical-electrical transforming means coupled to the material for transforming mechanical motions into electrical signals, wherein the improvement comprises a second displacement generator coupled to the material for applying a constant rate displacement to the material co-linearly with the cyclic displacement applied by the first generator.

Also provided is an improved apparatus for testing a viscoelastic material including (a) holding means connected to the material for holding the material in a predetermined position during testing;

(b) pretension means coupled to the material for applying tension to the material during testing;

(c) a first displacement generator having an eccentric means coupled to the material for applying cyclic displacement to the material;

(d) a second displacement generator having an eccentric means coupled to the material for applying cyclic displacement to the material co-directional with the cyclic displacement applied by the first displacement generator; and (e) mechanical-electrical transforming means coupled to the material for transforming mechanical motions into electrical signals, wherein the improvement which comprises a third displacement generator coupled to the material for applying a constant rate displacement to the material co-linearly with the cyclic displacement applied by the first and second displacement generators.

Further provided is an apparatus for testing a viscoelastic material to determine physical-structural properties of the material, adapted to differential testing of duplicate samples of the material, including:

(a) holding means connected to the material for holding the material in a predetermined position during testing;

(b) pretension means coupled to the material for applying tension to the material during testing;

(c) a first displacement generator having an eccentric means coupled to the first sample of the material for applying cyclic displacement to the material; and (d) mechanical-electrical transforming means coupled to the first sample of material, and mechanical-electrical transforming means coupled to the second sample of material, for transforming mechanical motions into electrical signals, wherein the improvement comprises a second displacement generator coupled to the first and second samples of material for applying a constant rate displacement to the first and second samples of material, wherein the displacement applied to the first sample is co-linear with the cyclic displacement applied by the first displacement generator.

Additionally provided is an improved process for testing viscoelastic material and measuring selected properties including:

(a) applying a cyclic first strain component to the material to be tested, being sinusoidal and having predetermined amplitude and frequency;

(b) transforming the stress resulting in the material from the strain applied into a composite electrical stress signal wherein the improvement comprises (c) applying a constant rate second strain component to the material to be tested.

Further, there is provided an improved process for testing viscoelastic material and measuring selected properties including:

(a) applying a cyclic sinusoidal first strain component to the material to be tested, having predetermined amplitude and frequency;

(b) simultaneously applying a sinusoidal second strain component to the material to be tested, having predetermined amplitude and frequency;

(c) transforming the stress resulting in the material from the strain applied into a composite electrical stress signal, the improvement which comprises (d) simultaneously applying a constant rate third strain component to material to be tested.

DESCRIPTION OF THE INVENTION AND PREFERRED EMBODIMENTS

Figure 1:
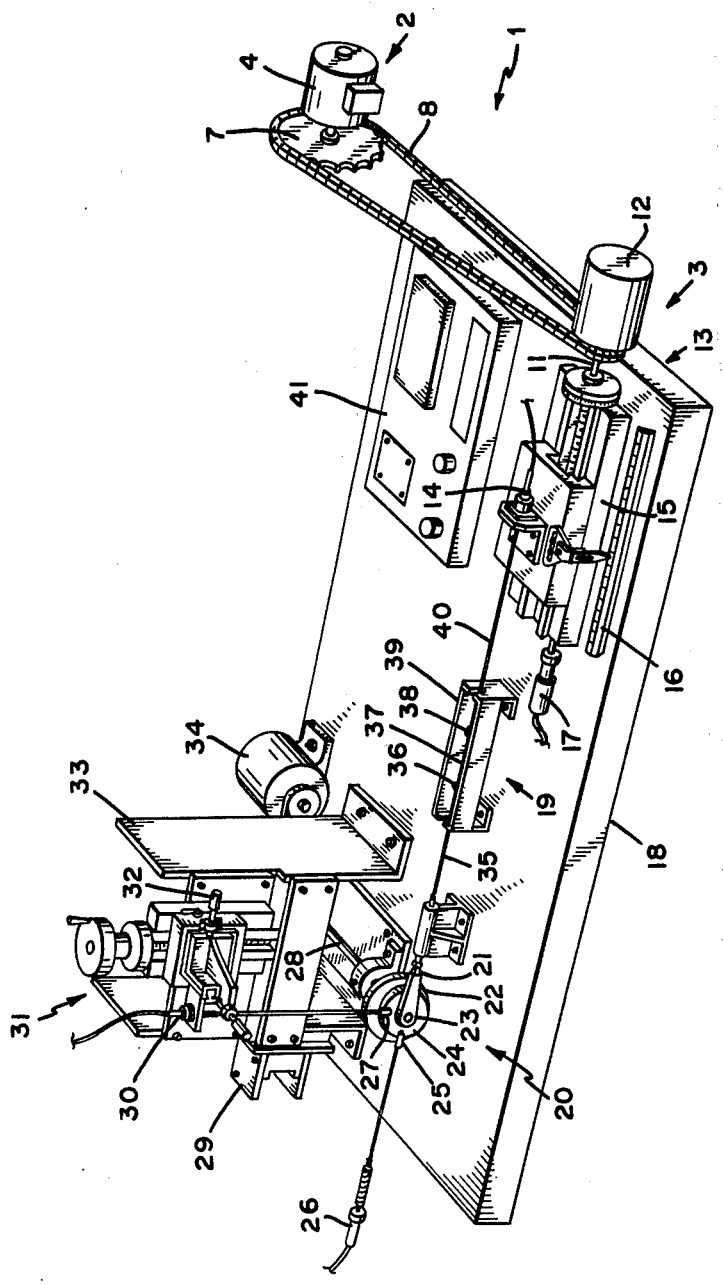
FIG. 1 is an isometric view of the apparatus of the present invention including a cyclic displacement generator and a constant rate displacement generator.

A description of the apparatus of the present invention can be readily made by reference to FIG. 1 which illustrates one embodiment of the invention apparatus including a holding means 19, pretension means 13, cyclic displacement generator 20, constant rate displacement generator 1 and mechanical-electrical transforming means 31 including first force transforming means 14, second force transforming means 26, third force transforming means 30 and position transforming means 17, coupled to the material.

Figure 2:
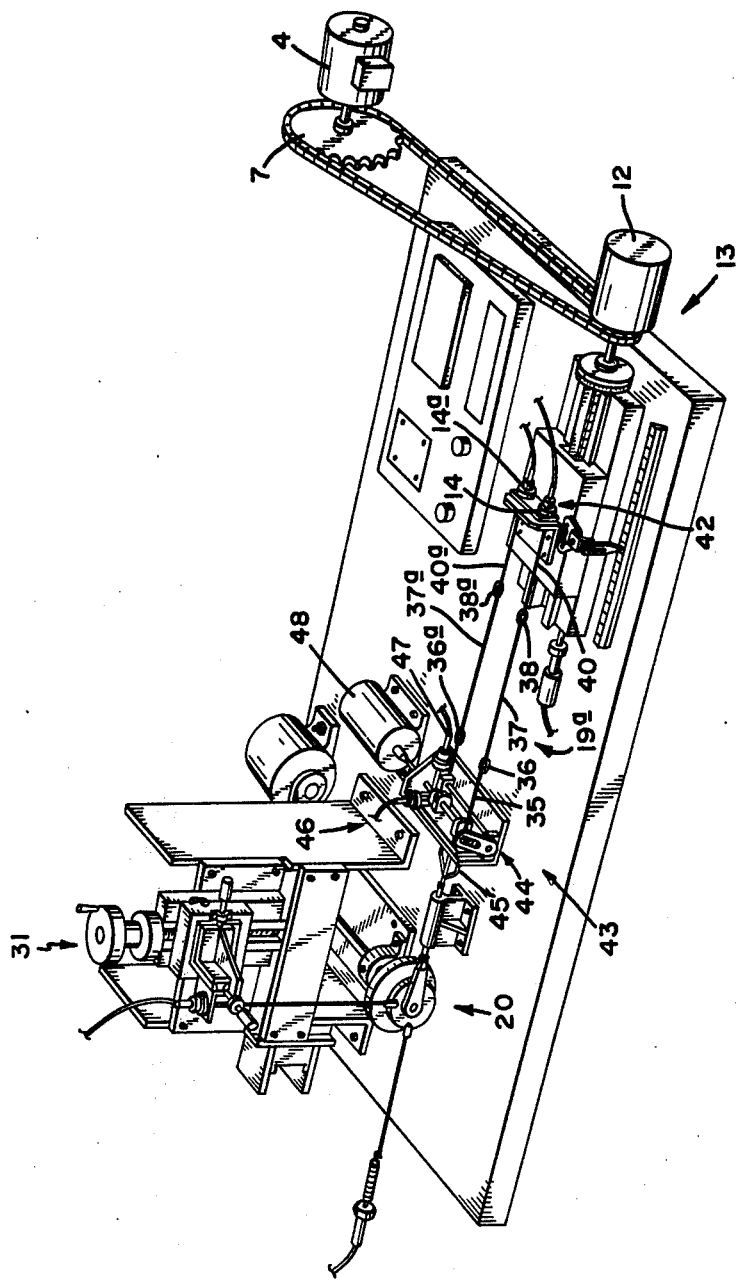
FIG. 2 is an isometric view of the apparatus of the invention further including a means for duplicate sample testing and a second cyclic displacement generator.

A further embodiment of the present invention apparatus is shown in FIG. 2, adaptable for duplicate sample testing or applying three or more strain displacements to a sample material, illustrating the constant rate strain generator 1, the cyclic displacement generator 20, a duplicate sample testing holding means 19a, and a third cyclic displacement generator 43, which optionally can be used when applying a constant rate strain displacement with at least two cyclic strain displacements superimposed thereon, to a sample material.

A description of the nature, operation and elements of the holding means 19, pretension means 13, cyclic displacement generators 20 and 43 and mechanical-electrical transforming means 31 of the apparatus, including duplicate testing holding means 19a, as well as processes and apparatus for measuring viscoelastic properties of materials, utilizing one and two cyclic displacement generators, have been adequately described in detail in the above-identified references of U.S. Pat. No. 3,969,930 and U.S. Pat. No. 4,056,973, the disclosures of which are hereby incorporated by reference.

As illustrated in FIG. 1, the function of holding means 19 is to position and maintain sample material 37 in a predetermined manner during the testing and includes two substantially rigid structural members, preferably two lengths of stiff wire, active wires 35 and 40. One end of each active wire has an engaging hook 36 or 38 for engaging the sample material 37 which is usually formed as a knotted loop. The other ends of the active wires are connected to the displacement generator 20 or to the pretension means 13. The furnace 39 serves as a temperature-chamber in which the sample can be heated to a particular desired temperature during testing. For duplicate testing, the holding means 19 also comprises duplicate testing holding means 19a including two mounting means on mounting bracket 44 for the first and second samples, 37 and 37a, respectively, and an additional mounting means 14a on bracket 42 of pretension means 13 as illustrated in FIG. 2.

The pretension means 13 serves two functions: one, to stretch sample material 37 longitudinally into a fixed flexible position at a certain pretension value, preferably a constant value, and to maintain that value during testing despite any "creep", in the sample, and two, to transmit the displacement generated by generator 1 to the sample, by means of mechanical means 3 including engaging screw 11, when generator 1 is coupled to the pretension means 13. The pretension means 13 includes an engaging screw 11, servo motor 12, strain gauge and transducer 14 (first force transforming means), carriage 15, scale 16, and linear variable differential transformer 17. The pretension means 13 is utilized for maintaining sample length during the application of periodic constant strain displacement, but is only utilized for this function at the beginning during unidirectional constant strain-to-rupture testing, for applying an initial pretension to the sample, since constant sample length is not maintained, during this particular testing.

The cyclic generator 20 includes a strain mounting means 21, a flywheel 22, eccentric means 23, linkage panel 24, second force transforming mounting means 25, third force transforming mounting means 27, shaft 28, switch housing 29, micropositioner 32, vertical frame 33 and generator motor 34, and serves to impart a cyclic displacement, usually sinusoidal, to the sample.

The mechanical-generator transforming means 31 serves to detect the strain, differentiated strain and resulting stress waves in the material, as a result of the known applied strain, and to convert the stress and strain waves into electrical signals and includes a first force transforming means 14, a second force transforming means 26 and a third transforming means 30 (in duplicate sample testing, a fourth force transforming means 14a is used and optionally, force transforming means 46 and force transforming means 47). The first transforming means 14 is a stress gauge and transducer, for transforming mechanical stress developed in the material into an electrical stress signal. The second force transforming means 26 is a strain gauge and transducer and is aligned 180° with respect to the first force transforming means 14 and transforms mechanical strain applied to the material into an electrical strain signal. The third force transforming means 30 is a differentiated strain gauge and transducer and positioned 90° with respect to the first and second transforming means and is a mechanical differentiating means which transforms a time derivative of mechanical strain applied to the material into an electrical cosine signal.

The cyclic generator 43 serves to produce a second cyclic strain component to the material and includes a mounting bracket 44, coupler 45, generator motor 48 and optional force transforming means 46 and 47.

The apparatus may also include an integrating means 41 for integrating a stress-strain hysteresis loop derived from the obtained electrical strain and stress signals, and may also include a display means (not shown) for displaying an output of the integrating means to measure the area of the stress-strain hysteresis loop and thereby determine energy loss during the expansion-contraction cycle.

The entire assembly is fitted onto a base means 18 such as a metal or wooden frame as illustrated in FIG. 1.

The novel feature of the present improved invention apparatus relates to the use of a constant rate strain displacement generator for studying viscoelastic properties of materials under applied constant rate strain. One embodiment of such a generator is depicted in FIG. 1, wherein the function of the constant rate generator 1 is to apply a constant rate displacement to sample 37 in a periodic manner, to cause a constant rate expansion-contraction cycle; or alternately, in a non-periodic unidirectional manner, thus causing the sample to expand and stretch longitudinally until rupture. The displacement applied by this generator is co-linear with the cyclic displacement applied by the cyclic displacement generator or generators, resulting in a fundamental constant rate strain displacement having cyclic, preferably sinusoidal, strain components superimposed thereon. In general, when the constant rate strain displacement is periodic, the cyclic displacement is of smaller amplitude and higher frequency than the constant rate periodic strain displacement. Preferably, the ratio of the frequency of the cyclic strain displacement to the frequency of the constant rate strain displacement is about 100:1. For example, if the frequency of the fundamental constant rate displacement is about 0.1 cps (cycles per second), then the applied superimposed cyclic frequency is about 10 cps.

When the constant rate strain is periodic or non-periodic, the strain amplitude of the applied cyclic displacement is preferably less than about 1% (one percent of sample length) and more preferably about 0.1 percent; and, the constant rate displacement is preferably applied at a constant strain rate of about 0.001 to 0.01 ($\Delta L/L$) per second.

The constant rate strain generator 1 includes a drive means 2 and a mechanical means 3. The drive means 2 provides a source of constant rate rotational power to mechanical means 2 which in turn, translates the rotational power into a constant rate displacement to sample material 37.

Figure 3:
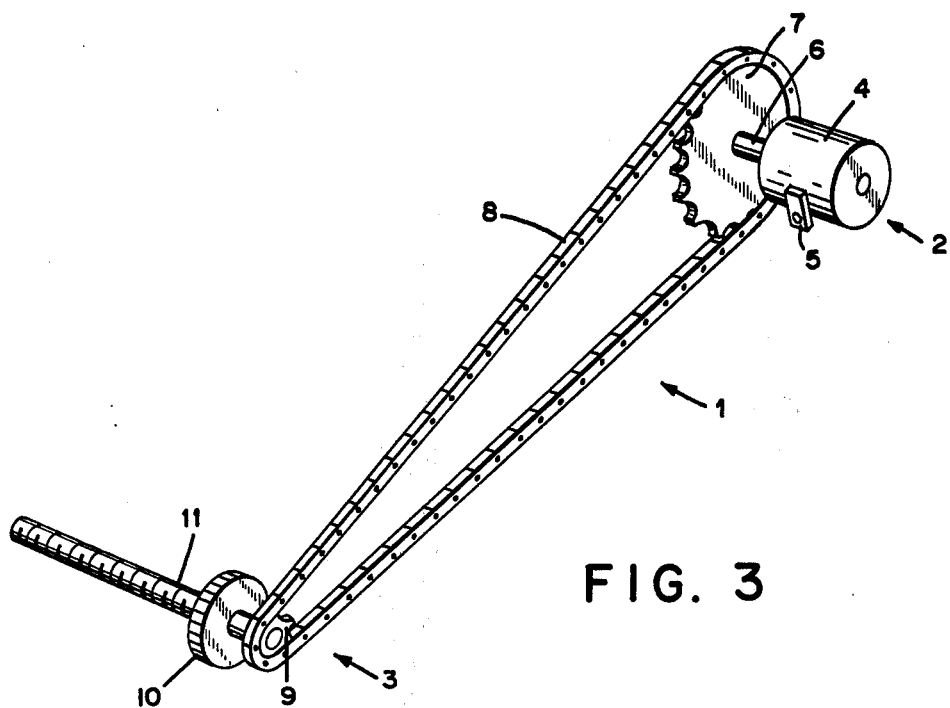
FIG. 3 is an isometric view of a constant rate strain generator (servomotor not shown).
Figure 6:
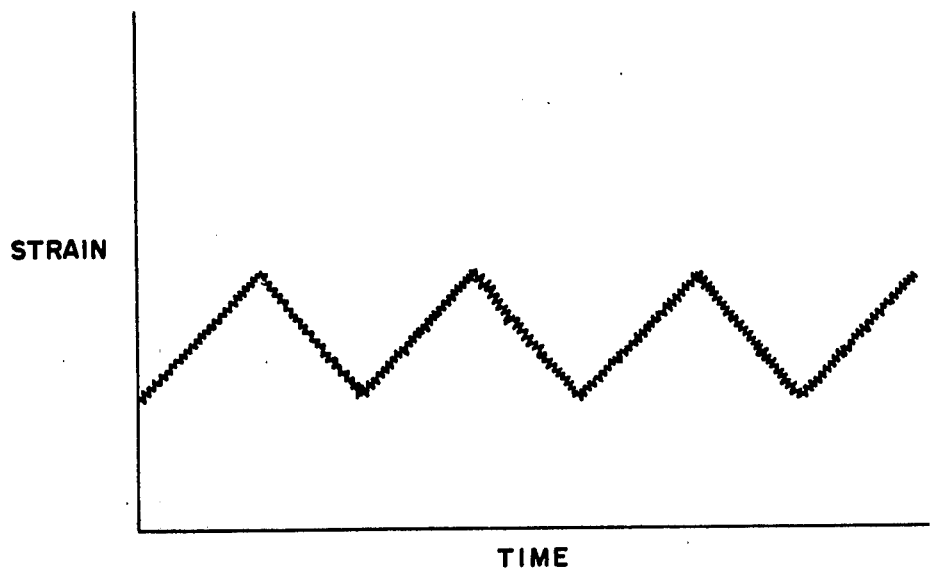
FIG. 6 is an illustration of an oscilloscopic display of periodic constant rate applied strain, with a high frequency small amplitude sinusoidal strain component superimposed thereon, plotted as applied strain versus time ("sawtooth strain wave").
Figure 9:
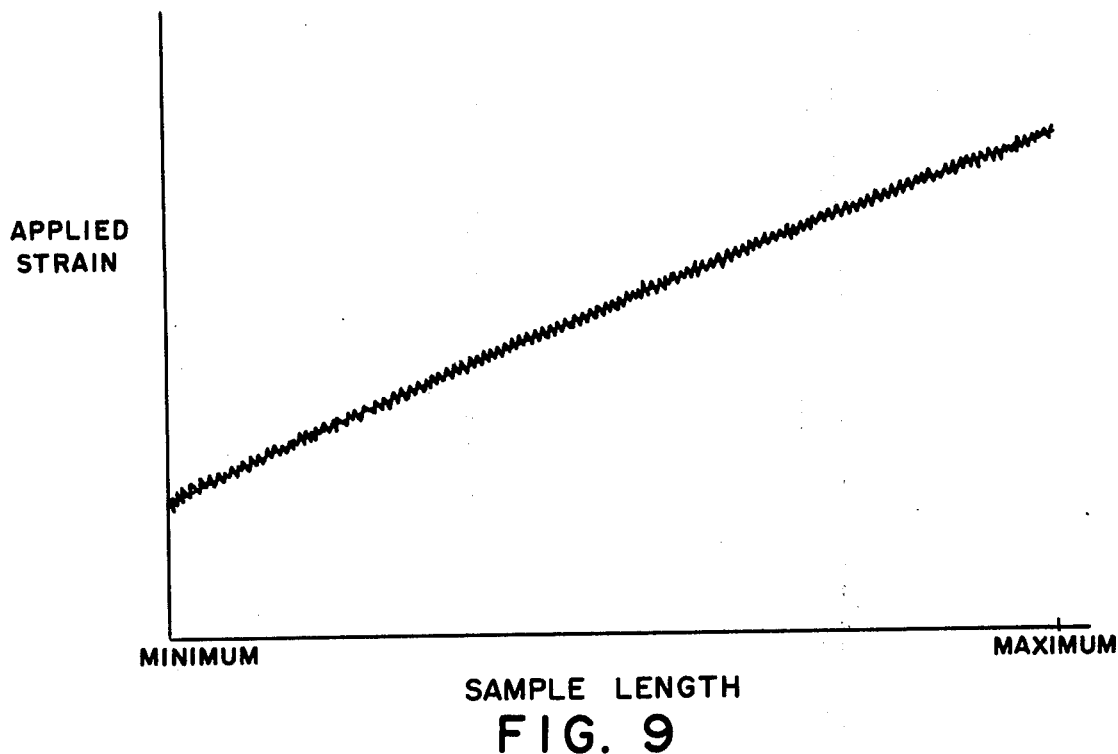
FIG. 9 is an illustration of non-periodic constant rate applied strain, with a high frequency small amplitude sinusoidal strain component superimposed thereon, plotted as applied strain versus sample length.

The drive means 2 includes a motor 4, speed and direction control means 5, drive shaft 6, driver sprocket 7 and chain 8. The speed and direction control means 5 regulates the speed and direction of motor 4, resulting in periodic or non-periodic applied displacement. In testing-to-rupture sampling, a constant rate displacement, having a superimposed high frequency sinusoidal component, is applied unidirectionally, in a non-periodic manner, as illustrated in FIG. 9, causing sample 37 to expand longitudinally until rupture. In periodic testing, speed and direction control means 5 regulates the speed and direction of the motor in a predetermined manner to achieve a constant rate periodic "saw-tooth" type of applied displacement as illustrated in FIG. 6, having a superimposed high frequency sinusoidal component, which total displacement is less than that required to rupture the sample. The motor 4 rotates drive shaft 6, which rotatably drives driver sprocket 7, which in turn drives chain 8. A sprocket-chain assembly as part of drive means 2 is shown in FIGS. 1, 2, 3; however, other assemblies such as a wheel-belt assembly are equivalent and operable in the invention.

Mechanical means 3 includes engaging screw 11 on which graduated dial 10 and driven sprocket 9 are mounted. Chain 8 is mated to driven sprocket 9 so that the rotational motion generated by drive means 2 is transferred to mechanical means 3 without loss of rotational motion through slippage. This is accomplished, for example, by means of teeth on driver sprocket 7 and driven sprocket 9 which mate with corresponding linkholes, for example, in chain 8. Driven sprocket 9 can also simply be the end of the shaft of threaded screw 11, as depicted in FIG. 3, or can optionally be, for example, a circular hollow piece firmly mounted onto the end of threaded screw 11 adjacent to servomotor 12. The rotational motion transferred to mechanical means 3 is translated into linear motion which drives carriage 15, by means of threaded member 11, connected to carriage 15 through engaging screw threads in a channel (not shown) on the underside of carriage 15. The resulting linear motion of carriage 15 is translated to sample 37, by virtue of the fact that sample 37 is mounted on carriage 15 under tension, to produce an applied constant rate displacement in a periodic or non-periodic manner. Graduated dial 10 indicates the amount of rotation of engaging screw 11 and the amount of movement of carriage 15 during testing.

Where only one cyclic displacement generator is used in conjunction with the constant rate displacement generator, both generators can be aligned on the same side of sample material 37 or can be preferably aligned on either side of the material as depicted in FIG. 1. In a preferred embodiment, the sample material is positioned longitudinally under tension, between the cyclic displacement generator and the constant rate displacement generator such that one generator is attached to one end of the material and the other generator is attached to the opposing end of the material. The constant rate generator 1 can be attached directly to the holding means 19 or can be attached in a preferred manner to the pretension means 13 as illustrated in FIG. 1. When attached to the pretension means, as depicted in FIG. 1, the rotational displacement generated by the constant rate generator 1 is translated into linear displacement and transmitted to carriage 15, by mechanical means 3, which directly transmits the applied linear displacement to mounted sample material 37.

Where differential duplicate sampling is desired, the apparatus as depicted in FIG. 2, including holding means, pretension means, cyclic displacement generator and mechanical-electrical transforming means coupled to each sample, can be employed where duplicate samples 37 and 37(a) are mounted to the mounting bracket 44, by a series of active wires 28 and 33 for sample 30, and 28a and 33a for sample 30a, coupled through hooks 29 and 31, and 29a and 31a, respectively. In this case the cyclic displacement generator 36 is not used to provide an additional superimposed cyclic displacement to the material, but the mounting bracket of the generator assembly is used as an aid in the holding means 19a for positioning both samples 37 and 37a and for transforming the cyclic displacement created by cyclic displacement generator 20 and constant rate generator 1. In duplicate testing, generator 1 is also utilized which applies a constant rate displacement to the first and second samples, while cyclic displacement, preferably sinusoidal, is applied to only the first sample. The apparatus further comprises a mechanical-electrical transforming means including force transforming means for transforming mechanical stress developed in the first sample by action of the first and second displacement generators into a composite electrical stress signal, and force transforming means for transforming stress developed in the second sample of material into an electrical stress signal. Thus, differential (duplicate testing) as well as non-differential testing can be performed by the apparatus.

If it is desired to apply a displacement comprising two or more cyclic components superimposed onto a fundamental constant rate component, then apparatus such as depicted in FIG. 2 can be utilized in which only one sample of material is utilized. In this case, generator 1 can deliver a periodic or non-periodic constant rate displacement and the apparatus can also comprise a plurality of cyclic displacement generators coupled to the material in which the cyclic displacement applied is co-directional with respect to each other, and is co-linear with the displacement applied by the constant rate generator. In addition, a plurality of constant rate generators may be employed for generating constant rate displacements, at different rates, co-linearly with each other and with the displacement applied by the cyclic generators, to the sample material.

Viscoelastic material which can be tested by the apparatus of the present invention includes mono- and multi-filament material, such as tire cord made of polymeric fiber and used for reinforcing pneumatic tires. Optionally, the solid to be tested may also be a yarn, fiber, rod or solid block of material. Primarily, the apparatus is used to test tire cord under simulated conditions which exist where a tire cord is in a tire running on a vehicle such as an automobile or truck. Included among properties tested for are ability of the tire fiber to withstand stress, strain and physical-structural fatigue and the apparatus is especially adapted to determine cyclic changes in the modulus and mechanical loss as a function of strain.

The present invention also includes an improved process for measuring viscoelastic properties of a material which comprises applying a constant rate strain component to the material to be tested, usually as a fundamental displacement, observing the resulting stress, then applying a cyclic strain component, preferably sinusoidal, of predetermined frequency and amplitude, preferably high frequency and low amplitude in relation to the constant rate component, superimposed onto the constant rate component and observing the resulting small stress response. The instantaneous modulus is then calculated from the ratio of the resulting small stress response amplitude to the superimposed cyclic strain. Integration of the modulus with respect to the strain yields the value of elastic stress at any given point of applied constant rate strain and is used to construct a curve of elastic stress corresponding to the curves of applied constant rate strain and observed stress. The phase angle difference, $\delta'$, is then calculated as the angle difference between observed stress and elastic stress, and is proportional to the mechanical loss.

The applied strain is either unidirectional, and is applied until sample rupture or is applied to a periodic constant strain rate below the rupturing force (maximum sample length). The mechanical stress resulting from the application of periodic constant rate strain is transformed into a composite electrical stress signal, and can be displayed electronically as part of a stress-strain curve wherein the resulting observed stress and applied strain wave forms are normalized to the same amplitude and can be electronically displayed or plotted as a resulting stress versus time curve as in FIG. 7.

The small stress response resulting from the application of a sinusoidal strain component superimposed onto a periodic constant strain wave can be displayed or recorded if desired, and the value of the instantaneous modulus and non-linear elastic stress can be calculated therefrom.

Figure 10:
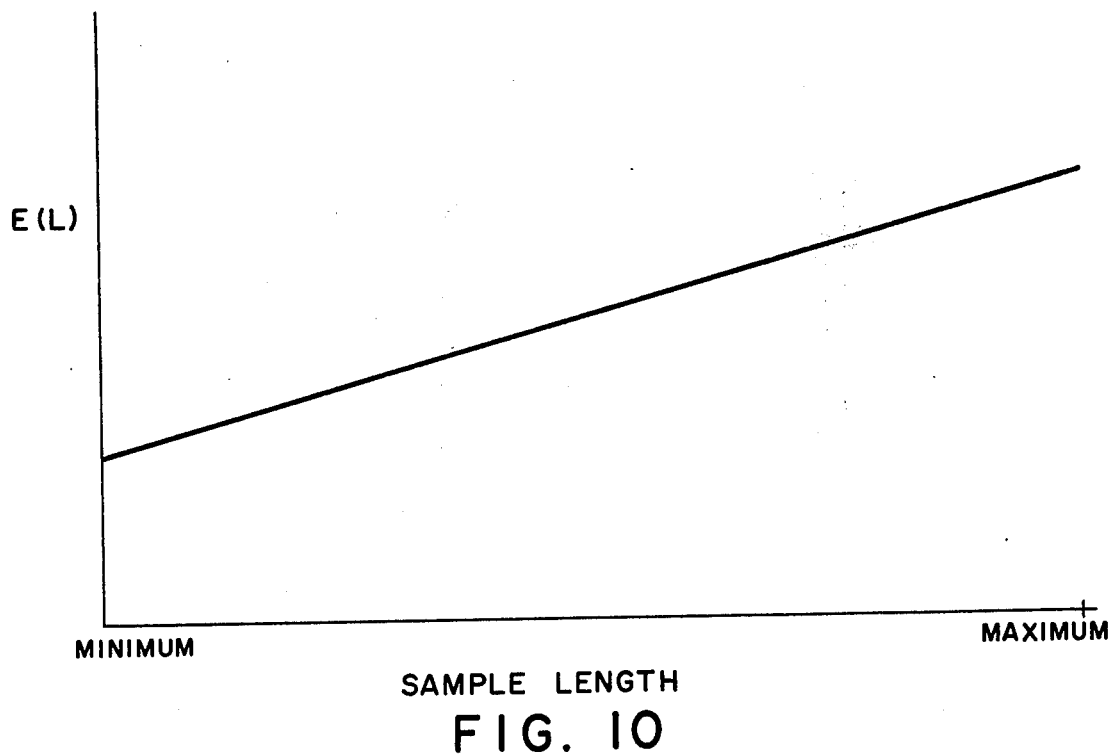
FIG. 10 is an illustration of the change in modulus, E(L), of a material, as a function of sample length (proportional to applied strain) during the application of a non-periodic applied strain as illustrated in FIG. 9.

The small stress response, resulting from the application of a sinusoidal component superimposed onto a unidirectional nonperiodic constant rate strain wave, as illustrated in FIG. 9, can be used to calculate the instantaneous modulus of the viscoelastic material during strain-to-rupture testing as a function of time and constant rate strain as illustrated in FIG. 10.

The process steps of applying a cyclic strain component to the material to be tested, being sinusoidal and having predetermined amplitude and frequency, and transforming the stress resulting in the material from the strain applied into a composite electrical stress signal includes the following individual steps of (a) positioning material sample in the holding means; (b) applying pretension to the sample and maintaining said pretension during testing by the pretension means; (c) applying a sinusoidal stress component to the material sample by means of one or two cyclic generators; (d) transforming the applied strain wave and resulting stress wave into composite electrical stress and strain signals; (e) displaying the electrical stress-strain signals on an oscilloscope and normalizing the amplitude heights; and (f) determining the modulus, the non-linear elastic stress, and the value of $\delta$ and $\delta'$, are all steps which are adequately described and disclosed in U.S. Pat. No. 3,969,930 and U.S. Pat. No. 4,056,973, supra, the disclosures of which are hereby incorporated by reference.

Figure 4:
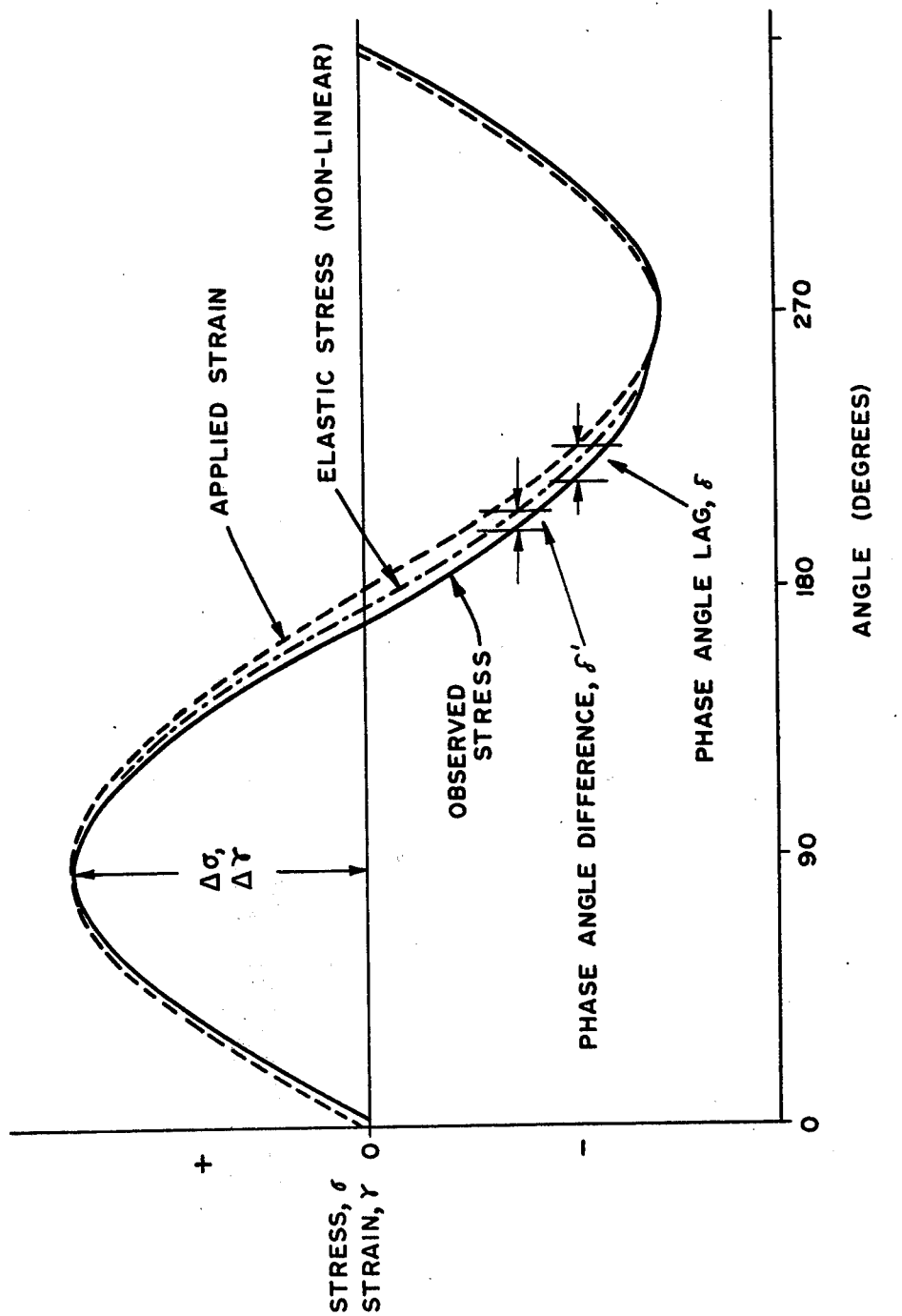
FIG. 4 is an illustration of normalized stress-strain variation in a typical viscoelastic material resulting from non-linear viscoelastic behavior plotted with reference to angle, showing the relationship of applied strain, observed stress, calculated non-linear elastic stress, phase angle lag, $\delta$, and phase angle difference, $\delta'$.

The novel feature of the present improved invention process is the application of a constant rate strain component, in a periodic or non-periodic manner, in addition to cyclic strain components, to the material to be tested and, by so doing, being able to determine the dependence of the parameter $\delta'$ upon the applied strain rate, and the instantaneous modulus of viscoelastic material during strain-to-rupture testing under a constant rate applied strain. As is seen in FIG. 4, the application of a sinusoidal strain component alone produces a normalized stress-strain curve from which it is impossible to measure the dependence of mechanical loss as a function of applied strain, since the applied strain rate is continuously varying.

A description of the invention process can be readily made by reference to FIG. 1 wherein sample 37 is positioned in the holding means 19, pretension is applied by pretension means 13, a constant rate strain component is generated by generator 1, the resulting strain is applied to the sample material, and the stress resulting in the material from the strain applied is transformed into a composite electrical stress signal.

A sinusoidal strain component is then generated by cyclic generator 20 and superimposed onto the constant rate strain component. The resulting small stress response is converted into a small electrical stress signal from which the instantaneous modulus and elastic stress can be calculated.

Preferably,, the cyclic strain component is applied to one end of the material, longitudinally stretched under tension, and the constant rate strain component is applied to the opposing end of the material co-linearly with the cyclic strain component.

The strain amplitude of the applied cyclic strain component is preferably less than about 1% (of sample length) and the constant rate strain component is preferably applied at a rate of about 0.001 to 0.01 ($\Delta L/L$) per second.

The cyclic strain component is of smaller amplitude and higher frequency than the constant rate strain component and preferably the ratio of the frequency of the cyclic strain component to the frequency of the constant rate strain component is about 100:1.

Figure 8:
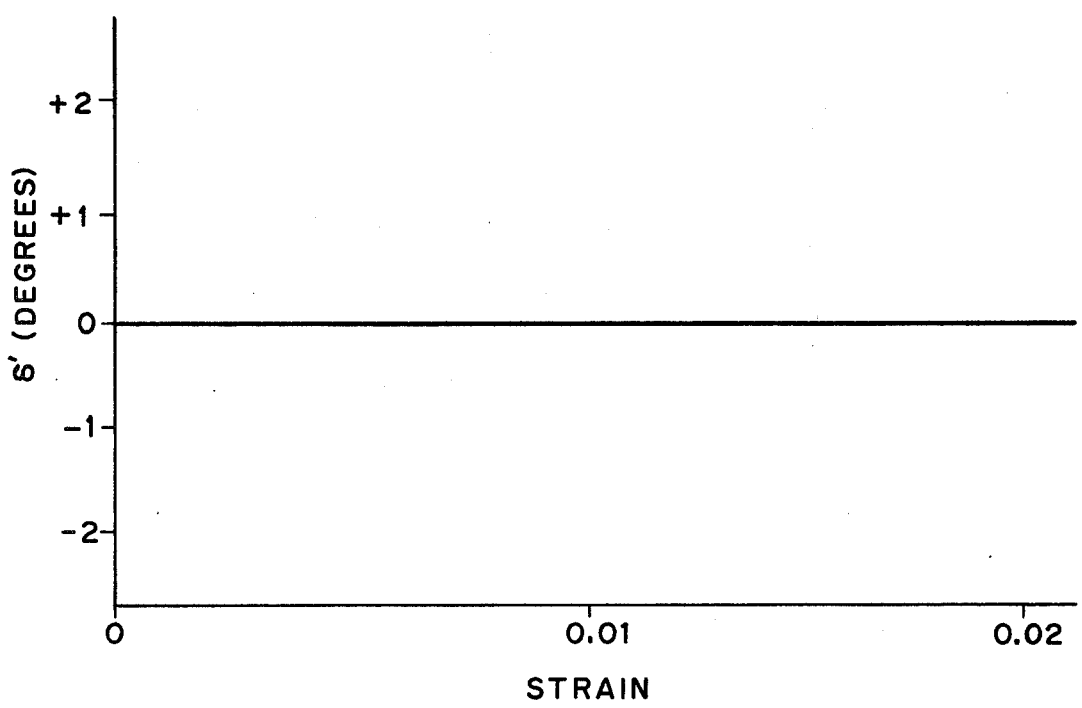
FIG. 8 is an illustration of the non-dependence of the phase angle difference, $\delta'$, on the applied strain and also strain rate during the application of periodic constant rate strain.
Figure 5:
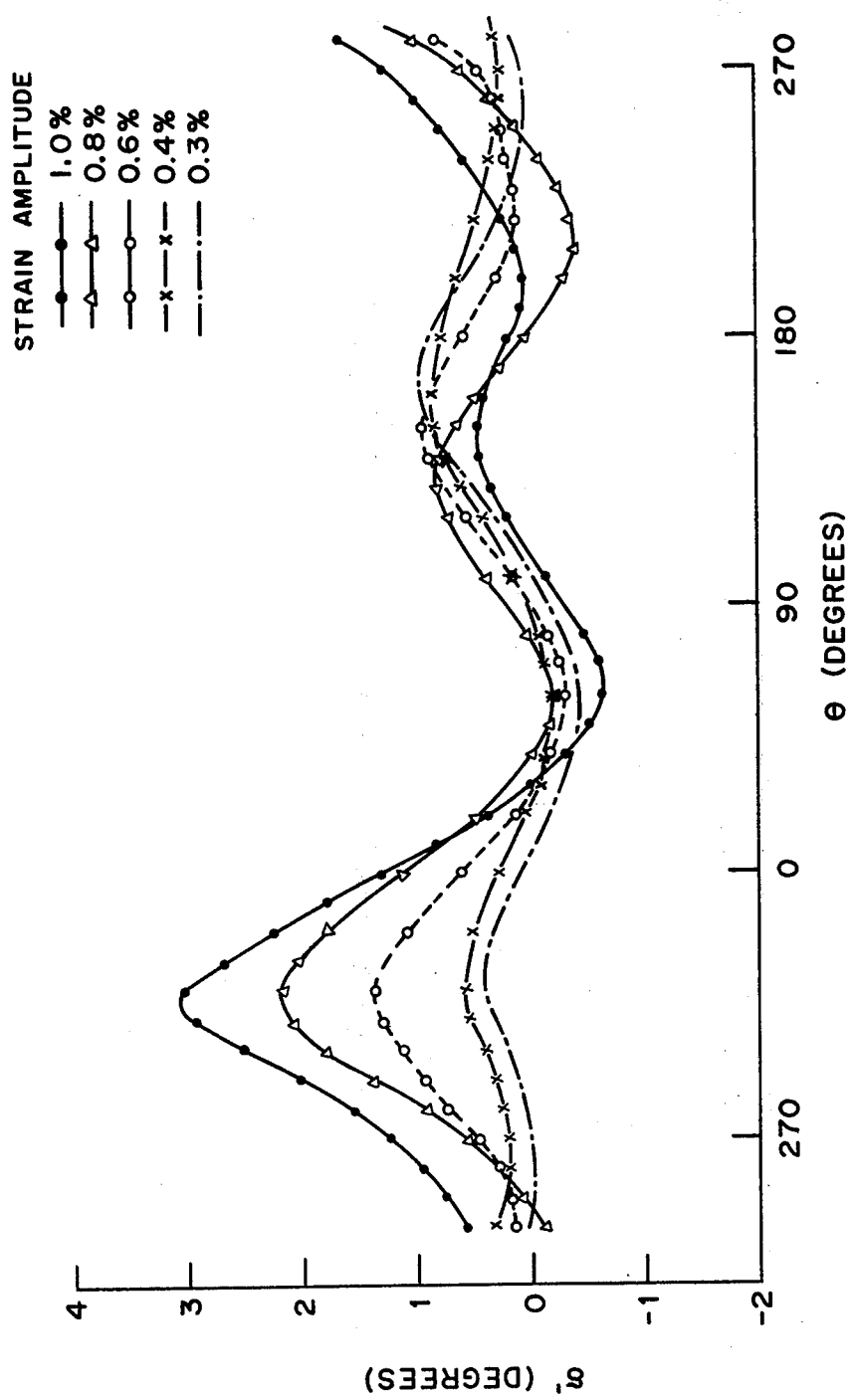
FIG. 5 is an illustration of the variation in $\delta'$ as a function of sinusoidally applied strain amplitude (from 0.3 to 1.0%) during a sinusoidal cycle for nylon-6 fiber at 25° C.
Figure 7:
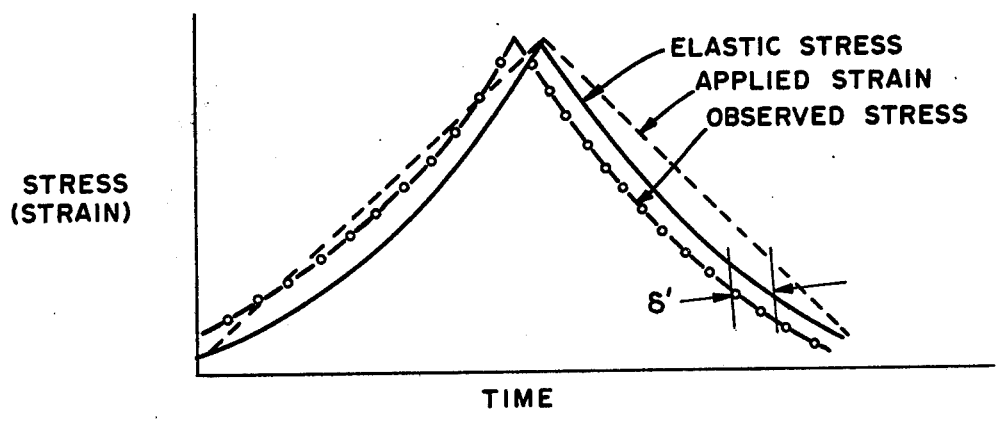
FIG. 7 is an illustration of observed stress, applied strain and calculated elastic stress plotted versus time for nylon-6.

To produce a periodic strain wave form, the constant rate generator 1 periodically generates a constant rate strain component in an alternating manner, and after displaying and recording the resulting observed stress, a very small amplitude high frequency cyclic strain component is superimposed thereon, thereby producing the "sawtooth" strain wave as illustrated in FIG. 6. This is applied to the sample material, and the resulting small stress response is used to calculate the nonlinear elastic stress wave form, from the instantaneous modulus, given by the relation $E = \Delta\theta/\Delta\gamma$. The applied constant rate strain, the observed stress and the non-linear elastic stress can be plotted for one cycle as illustrated in FIG. 7. Comparison of nonlinear elastic stress with the total observed non-linear viscoelastic stress curve yields, $\delta'$, the phase angle difference proportion to the mechanical loss, as illustrated in FIG. 7. Plotting $\delta'$ versus angle during applied sinusoidal strain at different strain amplitudes, as illustrated in FIG. 5, for example, as for nylon-6 fiber, shows that $\delta'$, the phase angle difference, varies as a function of the applied strain. However, by plotting $\delta'$, obtained by applying a constant rate strain component having a small amplitude high frequency sinusoidal strain wave superimposed thereon, versus strain, as illustrated in FIG. 8, shows that $\delta'$, for nylon-6, does not vary as a function of strain, where the applied strain rate is constant. Thus, the process enables one to determine the dependence of $\delta'$, for different viscoelastic materials, upon the rate of applied strain, and also values of $\delta'$ at different strain amplitudes.

To produce a non-periodic strain wave form as illustrated in FIG. 9, the constant rate strain generator 1 is driven unidirectionally, either clockwise or counter-clockwise at a constant rate and a high frequency, low amplitude sinusoidal strain component is superimposed onto the constant rate strain component. This strain is applied to the material continuously until sample rupture through expansion, and the instantaneous modulus can be calculated at any instant, from the observed small stress response, thereby yielding more information concerning the internal nature of the material during tensile testing. Preferably, two samples are run simultaneously, as in the process of duplicate testing, described below, wherein a constant rate strain is applied to both samples but only one having a small superimposed sinusoidal frequency superimposed thereon. This allows the observed stress, resulting from the large fundamental constant rate strain to be measured in one sample, and the instantaneous modulus to be measured from the other sample having the superimposed sinusoidal frequency thereon.

The improved process of the invention can also be adapted for testing of duplicate samples utilizing apparatus such as illustrated in FIG. 2 in which the cyclic strain component generated by cyclic generator 20 is applied to the first sample of material and the constant-rate strain component is applied to both the first and second samples of the material. The resulting stress is transformed into electrical stress signals which are displayed and compared and the differences in resulting induced stress behavior between the two samples can be noted.

Another embodiment of the invention process for testing viscoelastic material and measuring selected properties includes (a) applying a cyclic sinusoidal first strain component to the material to be tested, having predetermined amplitude and frequency; (b) simultaneously applying a sinusoidal second strain component to the material to be tested, having predetermined amplitude and frequency; (c) transforming the stress resulting in the material from the strain applied into a composite electrical stress signal and (d) simultaneously applying a constant rate third strain component to the material to be tested. By this method, another superimposed cyclic component is applied to the sample and the resulting stress yields further information concerning the modulus, mechanical loss and non-linear viscoelastic behavior of materials.

A further embodiment of the improved invention process includes applying a plurality of cyclic strain components to the material to be tested, being sinusoidal, having predetermined amplitude and frequency, and transforming the stress resulting in the material from the strain applied into a composite electrical stress signal wherein a constant rate strain component is simultaneously and additionally applied. By this particular process, further information regarding the modulus, mechanical loss and the non-linear viscoelastic behavior of materials can be obtained.

Another embodiment of the invention process further comprises applying a plurality of constant rate strain components to the material to be tested, which are co-linear with the cyclic displacements applied. Again, further information regarding the non-linear viscoelastic behavior of materials can be obtained.

The following examples are illustrative of the best mode of carrying out the present invention as contemplated by us but should not be construed as being limitations on the scope or spirit of the instant invention.

Example

Utilizing the apparatus of FIG. 1, a specimen loop made from a 20 cm. length of 2550 denier highly drawn nylon-6 monofilament was attached to the wires of the holding means. A pretension of 4 kg (force) was applied to the looped sample by the pretension means. A periodic constant rate strain of ±1% strain amplitude was applied to the sample, at a frequency of 0.05 cps. by the constant rate strain generator, resulting in a periodic, sawtooth-type fundamental strain. The resulting observed mechanical stress was transformed into a visual electronic signal on an oscilloscope and the amplitude of the stress wave was normalized to equal the amplitude of the applied strain wave. Both were displayed electronically. Values of observed stress, $\sigma$ data, were measured in units of dynes/cm$^2$ for different values of ($\Delta L/L$) as tabulated below for the expansion and contraction cycles.

Next, a sinusoidal wave having a relative amplitude of 5:1, and a relative requency of 200:1, as compared to the fundamental constant rate strain wave, was superimposed onto the fundamental wave by the cyclic strain generator resulting in a superimposed sawtooth type applied strain as illustrated in FIG. 6. The resulting small stress response, at the given percent strain amplitudes, was electronically observed, measured and recorded. The ratio of the small stress response to the small superimposed applied sinusoidal strain yielded the value of the instantaneous modulus, E(L) at a given percent strain point as illustrated in FIG. 9. Integrating the value of the calculated modulus with respect to the fundamental strain yielded the elastic stress, $\sigma_{el}$ of the nylon-6 fiber, at the given percent strain amplitude (see FIG. 7). Values of $\sigma_{el}$ are given below.

The difference between the two values, $\sigma_{data} - \sigma_{el}$ which is proportional to E', which in turn is approximatley proportional to the mechanical loss, was calculated for each strain point during the expansion and contraction cycles and is tabulated in the following Table. Positive values for $\sigma_{data} - \sigma_{el}$ are obtained for the expansion cycle and negative values are obtained for the contraction cycle due to the fact that the monofilament is undergoing non-linear viscoelastic behavior and there is a resulting phase lag between the observed elastic stresses. The magnitude of values is slightly different due to the requirement of normalizing $\sigma_{data}$ and $\sigma_{el}$.

TABLE

A. EXPANSION CYCLE

| Strain %, ΔL/L | $\sigma_{data}$ (dynes/cm$^2$) | $\sigma_{el}$ (dynes/cm$^2$) | $\sigma_{data} - \sigma_{el}$ |
|---|---|---|---|
| 0.0 | 0.00 × 10$^7$ | 0.00 × 10$^7$ | — |
| 0.4 | 4.665 " | 4.510 " | 0.155 |
| 0.8 | 9.952 " | 9.802 " | 0.150 |
| 1.2 | 15.239 " | 15.079 " | 0.160 |
| 1.6 | 20.713 " | 20.556 " | 0.157 |
| 2.0 | 26.373 " | 26.373 " | — |

B. CONTRACTION CYCLE

| Strain %, ΔL/L | $\sigma_{data}$ (dynes/cm$^2$) | $\sigma_{el}$ (dynes/cm$^2$) | $\sigma_{data} - \sigma_{el}$ |
|---|---|---|---|
| 2.0 | 26.559 × 10$^7$ | 26.559 × 10$^7$ | — |
| 1.6 | 20.558 " | 20.848 " | −0.260 |
| 1.2 | 14.913 " | 15.183 " | −0.270 |
| 0.8 | 9.579 " | 9.183 " | −0.275 |
| 0.4 | 4.571 " | 4.810 " | −0.269 |
| 0.0 | 0.000 " | 0.000 " | — |

As is seen from the data, the value of $\sigma_{data} - \sigma_{el}$ for nylon-6 monofilament remains essentially constant during either the expansion or contraction cycles under a constant-rate applied strain. Thus, for nylon-6 monofilament, both values of δ' during the expansion and contraction cycles are essentially constant during the application of a constant rate strain.

We claim:

1. In an apparatus for testing a viscoelastic material including
   (a) holding means connected to the material for holding the material in a predetermined position during testing;
   (b) pretension means coupled to the material for applying tension to the material during testing;
   (c) a first displacement generator having an eccentric means coupled to the material for applying cyclic displacement to the material; and
   (d) mechanical-electrical transforming means coupled to the material for transforming mechanical motions into electrical signals, the improvement which comprises a second displacement generator coupled to the material for applying a constant rate displacement to the material co-linearly with the cyclic displacement applied by the first generator.

2. The apparatus according to claim 1 wherein the strain amplitude of the cyclic displacement is less than about 1%.

3. The apparatus according to claim 1 wherein the constant rate displacement is applied at a rate of about 0.001 to 0.01 per second.

4. The apparatus according to claim 1 wherein the displacement applied by the second generator is periodic.

5. The apparatus according to claim 4 wherein the cyclic displacement is of smaller amplitude and higher frequency than the constant rate displacement.

6. The apparatus according to claim 5 wherein the ratio of the frequency of the cyclic displacement to the frequency of the constant rate displacement is at least about 100:1.

7. The apparatus according to claim 1 wherein the displacement applied by the second generator is non-periodic.

8. The apparatus according to claim 1 wherein the material is positioned longitudinally under tension between the first and second displacement generators such that the first displacement generator is attached to one end of the material and the second generator is attached to the opposing end of the material.

9. The apparatus according to claim 1 wherein the second displacement generator is coupled to the pretension means.

10. In an apparatus for testing a viscoelastic material including
    (a) holding means connected to the material for holding the material in a predetermined position during testing;
    (b) pretension means coupled to the material for applying tension to the material during testing;
    (c) a first displacement generator having an eccentric means coupled to the material for applying cyclic displacement to the material;
    (d) a second displacement generator having an eccentric means coupled to the material for applying cyclic displacement to the material co-directional with the cyclic displacement applied by the first displacement generator; and
    (e) mechanical-electrical transforming means coupled to the material for transforming mechanical motions into electrical signals, the improvement which comprises a third displacement generator coupled to the material for applying a constant rate displacement to the material co-linearly with the cyclic displacement applied by the first and second displacement generators.

11. The apparatus according to claim 10 wherein the displacement applied by the third generator is periodic.

12. The apparatus according to claim 10 wherein the displacement applied by the third generator is non-periodic.

13. The apparatus according to claim 10 further comprising a plurality of cyclic displacement generators coupled to the material for applying cyclic displacement to the material co-linearly with displacements applied by the first, second and third displacement generators.

14. The apparatus according to claim 10 further comprising a plurality of constant rate displacement generators coupled to the material for applying constant rate displacement to the material co-linearly with the displacements applied by the first, second and third generators.

15. In an apparatus for testing a viscoelastic material to determine physical-structural properties of the material, adapted to differential testing of duplicate samples of the material, including
(a) holding means connected to the material for holding the material in a predetermined position during testing;
(b) pretension means coupled to the material for applying tension to the material during testing;
(c) a first displacement generator having an eccentric means coupled to the first sample of the material for applying cyclic displacement to the material; and
(d) mechanical-electrical transforming means coupled to the first sample of material, and mechanical-electrical transforming means coupled to the second sample of material, for transforming mechanical motions into electrical signals, the improvement which comprises a second displacement generator coupled to the first and second samples of material for applying a constant rate displacement to the first and second samples of material, wherein the displacement applied to the first sample is co-linear with the cyclic displacement applied by the first displacement generator.

16. The apparatus according to claim 15 wherein the mechanical-electrical transforming means comprises
(a) force transforming means for transforming mechanical stress developed in the first sample of the material by action of the first and second displacement generators into a composite electrical stress signal; and
(b) force transforming means for transforming mechanical stress developed in the second sample of the material by action of the second displacement generator into an electrical stress signal.

17. In a process for testing viscoelastic material and measuring selected properties including
(a) applying a cyclic first strain component to the material to be tested, being sinusoidal and having predetermined amplitude and frequency; and
(b) transforming the stress resulting in the material from the strain applied into a composite electrical stress signal, the improvement which comprises;
(c) applying a constant rate second strain component to the material to be tested.

18. The process according to claim 17 wherein the strain amplitude of the cyclic strain component is less than about 1%.

19. The process according to claim 17 wherein the constant rate strain component is applied at a rate of about 0.001 to 0.01 per second.

20. The process according to claim 17 wherein the constant rate strain component is periodic.

21. The process according to claim 20 wherein the cyclic strain component is of smaller amplitude and higher frequency than the constant rate strain component.

22. The process according to claim 21 wherein the ratio of the frequency of the cyclic strain component to the frequency of the constant rate strain component is about 100:1.

23. The process according to claim 17 wherein the constant rate strain component is non-periodic.

24. The process according to claim 17 wherein the cyclic strain component is applied to one end of the material, longitudinally stretched under tension, and the constant rate strain component is applied to the opposing end of the material.

25. The process according to claim 17 wherein both strain components are continuously applied to the material until the material ruptures.

26. The process according to claim 17 adapted to differential testing of duplicate samples of material comprising:
(a) applying a cyclic first strain component to a first sample of the material to be tested, being sinusoidal and having predetermined amplitude and frequency; simultaneously applying a constant rate second strain component to the first sample of the material to be tested; and transforming the stress resulting in the first sample of the material from the strain applied by the first and second strain components into a composite electrical stress signal;
(b) applying the constant rate second strain component to a second sample of the material to be tested, and transforming the stress resulting in the second sample of the material from the strain applied by the constant rate strain component into an electrical stress signal; and
(c) generating a differential electrical stress signal representing the difference between the stress signals obtained from the first and second samples of the material.

27. In a process for testing viscoelastic material and measuring selected properties including
(a) applying a cyclic sinusoidal first strain component to the material to be tested, having predetermined amplitude and frequency;
(b) simultaneously applying a sinusoidal second strain component to the material to be tested, having predetermined amplitude and frequency;
(c) transforming the stress resulting in the material from the strain applied into a composite electrical stress signal, the improvement which comprises
(d) simultaneously applying a constant rate third strain component to material to be tested.

28. The process according to claim 27 further comprising applying a plurality of cyclic strain components to the material to be tested, being sinusoidal, having predetermined amplitude and frequency.

29. The process according to claim 27 further comprising applying a plurality of constant rate strain components to the material to be tested.

* * * * *